United States Patent [19]

Bencze et al.

[11] 4,172,447

[45] Oct. 30, 1979

[54] METHOD AND APPARATUS FOR INVESTIGATION OF GLAUCOMA IN EYE THERAPEUTICS

[75] Inventors: Jozsef Bencze; Jozsef Czine; Csongor Hegedus; Attila Kovats; Ferenc Nagy, all of Budapest, Hungary

[73] Assignee: Medicor Muvek, Budapest, Hungary

[21] Appl. No.: 723,073

[22] Filed: Sep. 14, 1976

[30] Foreign Application Priority Data

Nov. 17, 1975 [HU] Hungary .................. ME 1917

[51] Int. Cl.² .............................................. A61B 3/16
[52] U.S. Cl. .................................................. 128/648
[58] Field of Search ................... 128/2 N, 2 T; 73/80

[56] References Cited

U.S. PATENT DOCUMENTS

| | | | |
|---|---|---|---|
| 3,232,099 | 2/1966 | Motcheubacher | 73/80 |
| 3,246,507 | 4/1966 | Hyde | 73/80 |
| 3,572,100 | 3/1971 | Grolman et al. | 73/80 |
| 3,690,158 | 9/1972 | Lichenstein et al. | 73/80 |
| 3,871,360 | 3/1975 | Van Horn et al. | 128/2.05 R |
| 3,934,462 | 1/1976 | Reude | 73/80 |
| 3,992,926 | 11/1976 | Berryhill | 73/80 |
| 4,037,585 | 7/1977 | Gildenberg | 128/2 A |

OTHER PUBLICATIONS

*American Optical Non-Contact Tonometer — A Status Report,* 1976, Grolman, in Optical Engineering, Jul.-Aug. 1976.
*Miniature Passive Pressure Transensor for Implanting in the Eye,* Collins, IEEE Transactions on Biomed Engr., vol. BME 14, #2, Apr. 1967.
*Bailey's Histology,* Copenhauer, Bouge & Burge; Williams & Wilkins Co., 1971, pp. 664–667.
*Human Nervous System,* Barr; Harper & Row Publishers, Hagerstown, Md., 1972, p. 126.
*Physical Diagnosis,* Hochstein & Rubin, McGraw-Hill, N. Y., 1964, p. 364.

*Primary Examiner*—Robert W. Michell
*Assistant Examiner*—Francis J. Jaworski

[57] ABSTRACT

The apparatus of the invention comprises means for examining the human eye for the onset of glaucoma. The eye undergoing examination forms one plate of a virtual capacitor the other plate of which is formed by a gas nozzle. The body of the person undergoing examination and the gas nozzle are connected to the input of a signal converter the output of which is sampled at a predetermined instant by a sampling and sample-holding means. A gas jet from the nozzle is directed at the eye and a sample made of the output of the signal converter. An indicator connected to the sampling and sample-holding means provides a measurement of the deformation at the surface of the eye caused by the dynamic pressure of the gas jet. Sampling may be carried out at moments determined by the systolic rhythm of the person being examined. Preferably samples are taken at the systolic and diastolic moments thereof, the samples being compared to give an indication of the dynamic performance of the eye.

6 Claims, 8 Drawing Figures

METHOD AND APPARATUS FOR INVESTIGATION OF GLAUCOMA IN EYE THERAPEUTICS

BACKGROUND OF THE INVENTION

The invention relates to apparatus for examining eyes to detect the presence of absence of glaucoma therein. The apparatus includes means by which the level of the pressure of the aqueous humour which is inside the eye can be established and the disruption of the flow behaviour (which is brought about by a reduced functioning of the excretory ducts) can be detected. It is suitable for carrying out ophthalmodynamometric and ophthalmodynamographic examinations by means of the detection of the pulse pressure amplitudes of the aqueous humour.

Statistics show that glaucoma (aglaucopsia) affects 2 to 4% of adults more than 40 years old, but it is to be considered as a cause of blindness in 15 to 20% of cases. At the present time, glaucoma can still not be cured, but it can be discovered at an earlier stage and as a result the development of the disease can be remedied or delayed. An extensive examination of the population for glaucoma is therefore important, this being for the purpose of a successful treatment of the disease and for preserving vision as long as possible, particularly nowadays, because the average age is considerably extended.

The occurrence of glaucoma is signalled by a pathologically increased pressure of the aqueous humour. The accepted physiological upper limit of the aqueous humour pressure with a healthy eye is 21 mm Hg. A pressure of 22 to 26 mm Hg already indicates the suspicion of glaucoma, and a pressure value higher than 26 mm Hg means the certain pathological state of the eye. For those cases which are not certain, diagnosis can be achieved by varying the volume of the aqueous humour, which effect can be produced by means of a pressure exerted on the eye for a few minutes. By determining the amount of the aqueous humour which escapes or by noting the variation of the pressure, it is possible to detect an upsetting of the equilibrium between the production and the excretion, i.e. a disruption of the excretion process. According to the most recent test results, and also in the case when the physiological aqueous humour pressure is normal, this points to the presence of glaucoma.

The processes which serve for measuring the pressure of the aqueous humour are known as tonometry, and those processes which serve to detect a disruption in the excretion process or a variation in time required for the aqueous humour pressure to change are known as tonography.

It is possible with a live person directly to establish the pressure of the aqueous humour in the eye by opening the eye. However, apart from a few special operational cases, this is not advisable. A process has therefore been widely used, according to which the actual pressure of the aqueous humour is determined indirectly, according to the tension of the eye sheaths. However, this means that the results of the measurements are influenced in a given case by the physical properties of the cornea and of the sclera, which differ, depending on the person. Summarising, these properties are known as "rigidity".

The prior known tonometric processes can be divided into two groups: these are the impressionisitic tonometry and the aplanatic tonometry.

Using impression tonometry, the pressure of the aqueous humour is detected by the extent of penetration of a given load, which is exerted on the surface of a few square millimeters of the cornea. The degree of penetration is then made visible by means of an appliance and an indicating instrument, which is operated either by mechanical transmission or by means of a measurement signal converter.

With the aplanatic tonometry, the pressure of the aqueous humour is detected by a load which is necessary for achieving a specific surface. Used for observing the aplanation surface is a conventional optical device and the loading and the indication thereof are obtained by mechanical means. Using the aplanation process, the pressure of the aqueous humour can be established in more accurate manner and with less influence caused by the rigidity, but the impression process is also suitable for carrying out tonographic measurements.

Both processes have one particular disadvantage, which is of main significance with mass examinations, and this is that the measuring head which comes into contact with the eye is able to cause an epidemic and a disease of the sclera and cornea. For the purpose of avoiding this, the measuring head is to be cleaned or disinfected before each examination, but this is very comlicated and time-consuming and cannot always be carried out with success. The mass examinations accordingly have to be stopped (frequently for several months), more especially at the time of an epidemic. An additional disadvantage of the known devices consists in that the examination requires a local anaesthetic and the cornea can be easily damaged during the measurement.

These disadvantages can simply be overcome by a process, which is associated with the aplanatic tonometry, in which the measuring head does not come into contact with the eye, but the deformation of the eye is caused by a stream of air or gas which is blown on to the surface of the eye and which has a linearly increasing speed as a function of time. The instantaneously aplanated surface (which has a diameter of about 3.6 mm) is indicated by means of a light beam which is projected on to the eye and is reflected back from said eye. The pressure of the aqueous humour is determined by the period of time which meanwhile elapses. However, this method suffers from the disadvantage which consists in that the pressure of the aqueous humour fluctuates according with the pulse cycle, as a result of which the measurement is considerably influenced. The pressure fluctuation caused by the pulse amounts to 2-3 mm Hg. Such a pressure fluctuation masks the examination results, especially in boundary cases.

It is a primary object of the invention to eliminate said defects and disadvantages of the known devices. It is a further object of the invention to provide a comparatively simple apparatus which does not come into contact with the eye during the examination. It is yet a further object of the invention to provide more accurate measurement by the elimination of the pulse effect. It is yet a further object of the invention to provide apparatus which is equally suitable for tonographic and tonometric measurements, and for carrying out ophthalmodynamometric and ophthalmodynamographic examinations.

SUMMARY OF THE INVENTION

The above and other objects of the invention are attained by utilising a process wherein the pressure of the aqueous humour is established by deforming the surface of the eye by means of a jet of air, or an inert gas or a mixture thereof, blown onto the eye, the deformation produced by the dynamic pressure of the gas being measured by the change in capacitance of a measuring capacitor, of which one electrode is the surface of the eye.

This process can also be carried out in such a way that the measurement takes always place in the systolic and/or in the diastolic points of the pulse pressure curve of the aqueous humor. This can be performed by synchronizing the measurements to the systolic and/or diastolic points of a peripheral pulse curve scanned by a pulse sensor, which is placed on the body close to the eyes. From the differences of the deformation values measured at the systolic and at the diastolic points of the pulse pressure curve of the aqueous humor, conclusions can be drawn to the dynamic behavior of the eye. Apparatus according to the invention which serves for carrying out the process as thus explained is constructed in such a way that a measuring capacitor is connected to one input of a measuring converter which converts the change in capacitance to an electric signal, the output of the measuring converter is connected to an input of a sampling and holding circuit, while the output of the latter is connected to the indicating or recording instrument. An output of a control unit is connected to the other output of the sampling and holding circuit, and also to the input of the pneumatic system serving to produce the gas stream or jet. The device can be constructed in such a way that the measuring capacitor is connected to the input of the measuring converter, the output of the later is connected to an input of the sampling and holding circuit, and the output of the sampling and holding circuit is connected to an input of an arithmetic system, in order to produce signals which are proportional to the measured deformation values, or serves for forming their averages and/or differences. Connected to the input of the analyser circuit is the output of the pulse sensor or of the measuring converter. The output of the analyser circuit is connected to the input of the control unit. One output of the control unit is connected to the other input of the arithmetic system, while the other output thereof is connected to the other input of the sampling and holding circuit, while its third output is connected to the input of the pneumatic system or unit which serves to produce the air or gas stream.

BRIEF DESCRIPTION OF THE DRAWINGS

The method and apparatus according to the invention are illustrated by and are explained by reference to, the accompanying drawings, in which.

DETAILED DESCRIPTION OF THE METHOD OF THE INVENTION AND PREFERRED EMBODIMENTS OF APPARATUS ACCORDING THERETO

Figure 1:
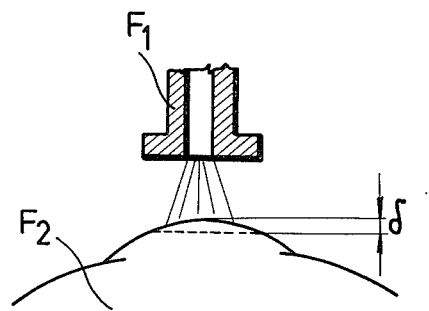
FIG. 1 illustrates the blowing of the air or gas stream on to the cornea of the eye.
Figure 2:
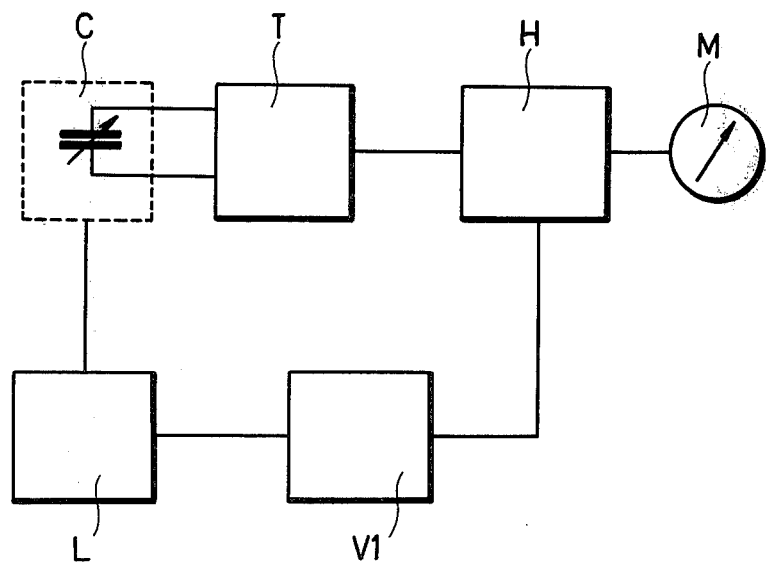
FIG. 2 illustrates the circuit arrangement of the device.

The essence of the invention is to be understood by reference to FIGS. 1 and 2. The deformation of the cornea is produced by a dynamic jet of air or other gas, or a mixture thereof, which is emitted from the nozzle F1. The nozzle is arranged at an appropriate distance from the eye and the air or the gas is discharged either at a constant velocity or at a velocity which is variable as a function of time. The deformation $\delta$ is observed by a capacitative transmitter. One of the electrodes of the measuring capacitor C of the capacitative transmitter is formed by the nozzle F1, which is either made of a conducting material or of a dielectric material having a conducting coating. The surface of the nozzle, which is shown as flat, is a matter of choice. It may also be convex or concave. The other electrode F2 of the measuring capacitor C is formed by the surface of the eye. Because of the deformation $\delta$, the original capacitance $C_o$ of the said condenser is changed and in fact by a value $\Delta C$ which is proportional to the penetration.

The conversion of the variation $\Delta C$ of the capacitance into electric signals is effected by means of known circuits (bridge circuit, frequency modulation) in the measuring converter circuit T. Consequently referring to FIG. 2, the device is actuated in the following manner:

The control unit V1 starts the pneumatic system or unit L and after the play-back of the transients, emits a sampling order to the sampling and holding-current circuit H. The sample and holding circuit H switches the sample or specimen derived from the output signal of the measuring converter T to the indicating instrument M and the control unit V1 switches off the pneumatic unit L.

By a suitable development of the arrangement according to the circuit diagram of FIG. 2, an electrical signal of sufficient amplitude can be produced which is proportional to the deformation of the eye within the range of a few tenths of a millimeter. With such the result can easily be achieved that an electric signal which can be estimated and also a deformation $\delta$ of a few tenths of a millmeter are produced. With such a small deformation, the measurement result is influenced to a lesser degree by the rigidity of the eye, which rigidity can differ depending on the person. At the same time, the measurement can be effected in a fraction of a second. No anaesthesia is to be applied if a single air puff is used and the volume of the aqueous humour is also not changed during the measurement. The proposed arrangement is therefore suitable for carrying out tonometric examinations, but is particularly suitable for tonometric mass examinations.

The effect of the pulse wave influencing the measurement is avoided if the measurement of the deformation of the cornea is carried out at the specific points of the pulse pressure curve of the aqueous humor that is at the systolic and/or at the diastolic points, or in the points of the pulse pressure curve of the aqueous humour which are located at a specific position and in fact at the systolic and/or diastolic points, or in the immediate vicinity thereof. This is effected in such a way that the pulse curve is scanned at a given point of the body surface by means of a suitable sensor. The time instants of the deformation measurement of the cornea are synchronised with the indicated points of this curve, advantageously with the systolic and/or diastolic points. If the scanning of the pulse curve takes place at a position close to the eye no time shift appears between the peripheral pulse curve and the pulse pressure curve of the aqueous humor, and the measurement synchronized to the systolic and/or diastolic points of the peripheral pulse curve provides the systolic and/or diastolic pressure value of the aqueous humor. the difference of the systolic and diastolic pressure of the aqueous humor (the amplitude of the pulse pressure wave) has also a diagnostic significance mainly from the point of view of ophthalmodynamographic and ophthalmodynamometric measurements. If the pulse sensor is arranged at a more distant point in relation to the eye, then a time shift resulting from the speed of the pulse wave occurs between the pulse curve and the position of the aqueous humour pressure. With the measuring arrangement as proposed, this time shift has the least effect on the mean of the value measured in the systolic and diastolic moments of the peripheral pulse curve; the said average value; the said measurement result can consequently be used for diagnostic purposes.

Serving to carry out the measurement process is an arrangement according to the invention which is illustrated by reference to the circuit diagram shown in FIG. 3. From the pulse curve, which originates from the output signal of the measurement converter T, or is generated by the pulse sensor P (see FIG. 4), the analyser A determines the time moments $t_1, t_2, t_3$... etc. which correspond to the systolic $P_S$ and/or diastolic $P_D$ values of the peripheral pulse curve and transmits at this moments synchronizing and identifying signals to the control unit V2. After starting up the pneumatic unit L at the instant $t_o$ (see FIG. 4b), the control unit V2 receives the synchronous or identifying signals and emits in the systole and/or diastole instances a sampling order to the sampling and holding circuit H. The sampling and holding circuit H transmits the sample derived from the signal of the measuring converter T to the computing unit K. Depending on the order or instruction of the control unit V2, the computing unit K carries out the following functions: it switches the electric signal which are proportional to the aqueous humour pressure (occurring at the moments in the systole and/or diastole), or the average value thereof, to the indicating instrument M. With the formation of the difference of the signals proportional to the aqueous humour pressures (pressures occurring at the moments of the systole or diastole), it then produces the pulse pressure wave amplitude and switches this to the indicating instrument M. If the control unit V2, after measuring a systole and a diastole value, switches off the pneumatic unit (see FIG. 4b, instant $t_o'$), it also becomes suitable for ophthalmodynamometric or ophthalmodynamographic measurements. If the control unit V2 only switches off the pneumatic unit L after the measurement of several systole and/or diastole values (see FIG. 4c, instant $t_o$), then the device, by determining the change in volume of the aqueous humour during the loading, or by determining the variation in pressure of the aqueous humour, is also suitable for carrying out tonographic examinations. In accordance with another example, the surface of the eye is not loaded by a continuous dynamic pressure. It is simply loaded in impulse fashion, and in fact in the immediate vicinity of the systole and/or diastole values, in order to produce the deformation. This process means a smaller stressing for the person being examined. but at the same time higher standards are required of the device for carrying out the measurement process.

Figure 3:
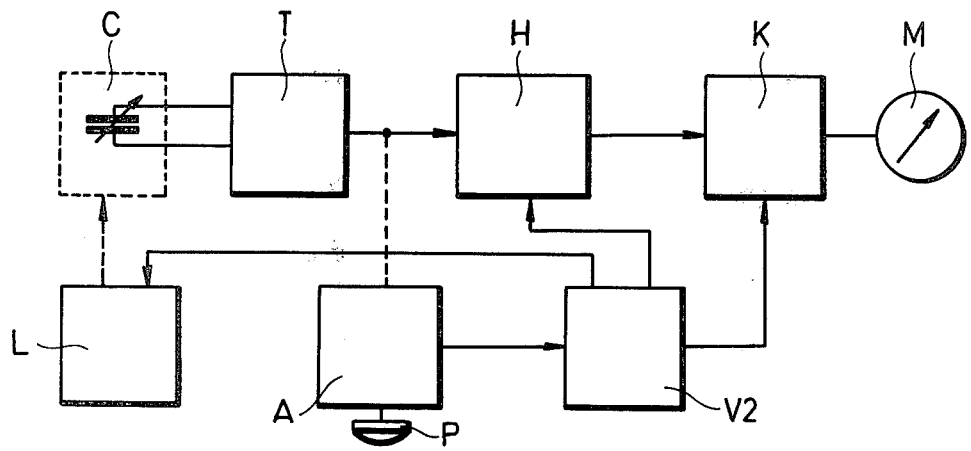
FIG. 3 illustrates another constructional example of the arrangement, based on its circuit diagram, and FIGS. 4a–4e indicate the pulse curves.

The process which uses the loading applied in pulse-like manner is explained by reference to an arrangement which is shown in FIG. 3, of which the circuit arrangement is illustrated by means of the diagrams given in FIGS. 4a, 4d and 4e.

The analyser A "observes" the ascending flank of the signal curve which is picked up by the pulse sensor P or transmitted by the measurement converter T and transmits a "prepare signal" to the control unit V2 at a moment existing before the systole value is reached (see FIG. 4a, instant $t'_1$) and preferably at an instant which belongs, for example, to the inflection point of the curve. The pneumatic unit L is started by the control unit V2 (see FIG. 4d, instant $t'_1$) and thereafter receives the synchronising or identifying signals generated by the analyser at the instant of forming the systole value and sends a sampling order to the sampling and holding circuit H. After the sample has been taken, the pneumatic unit L is switched off by the control unit V2 (see FIG. 4d, instant $t''_1$). In a similar manner, the analyser A "observes" the descending flank of the pulse curve and, at a moment before the diastole value is reached (see FIG 4a, instant $t'_2$) preferbly at a moment belonging to the influsion on the inflexion point of the curve, transmits a "preparatory" signal to the control unit V2. The pneumatic system or unit is once again started by the control unit V2 (see FIG. 4d, instant $t'_2$), thereafter receives the synchronising or identifying signals sent by the analyser A at the moment of producing the diastole value and delivers a sampling order to the sampling and holding circuit H. After taking the sample, the control unit V2 switches off the pneumatic unit L (see FIG. 4d, instant $t''_2$).

The arrangement which has been discussed by reference to FIGS. 3, 4a and 4d, with the establishment of the aqueous humour pressure, which occurs at a moment in a systole and/or in a diastole, is suitable for carrying out tonometric examinations. If the aqueous humour pressure is established both in the systolic moment and also in the diastolic moment, the device is also suitable for carrying out opthalmodynamometric or ophthalmodynamographic measurements.

Figure 4A:
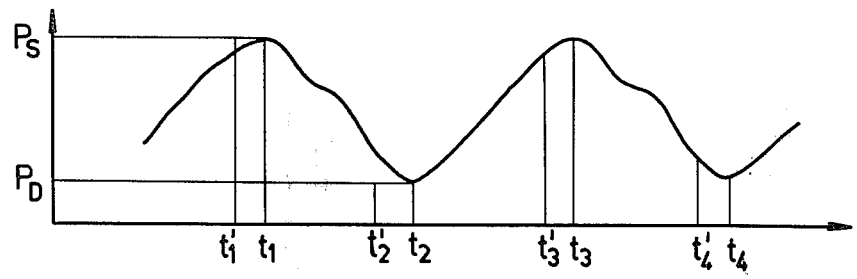
Figure 4B:
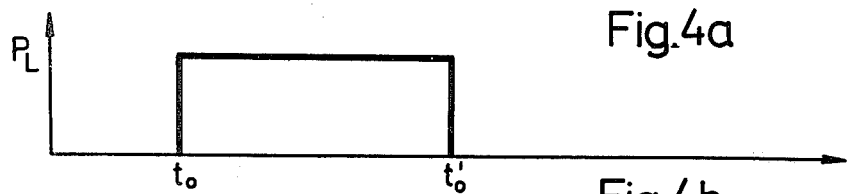
Figure 4C:
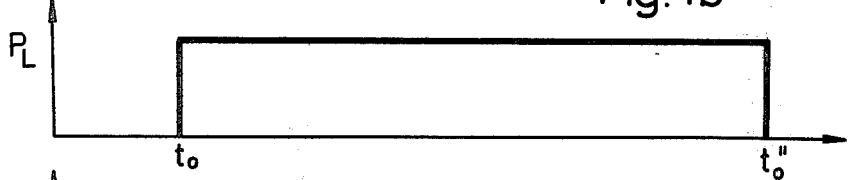
Figure 4D:
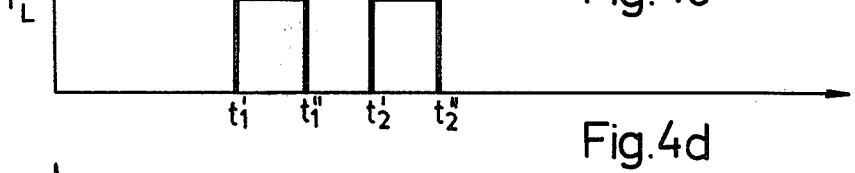
Figure 4E:
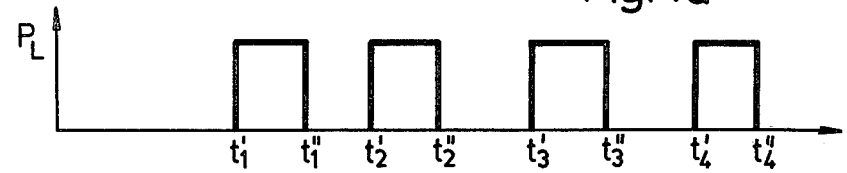

When the processing steps of the measuring procedure according to FIGS. 3, 4, 4a or the functioning of the device serving for carrying out such measurements are repeated several times, that is to say, the measurement of the aqueous humour pressure is synchronised to the systolic and/or diastolic values, it is possible for the pulse-like loading of the eye surface to be established (see in this connection FIG. 4e, pressure pulses at the moments $t'_1, t''_1, t'_2, t''_2, t'_3, t''_3, t'_4, t''_4$... etc.). As a consequence, the device is suitable for detecting the disruptions in excretion of the aqueous humour and for carrying out tonographic measurements. The advantage of the process which is proposed in connection with FIGS. 3, 4a and 4c and suitble for measuring tonographic measurements, and of the device suitable for carrying this process into effect, consists in that the time required for the measurement can be considerably shortened and that mass examinations can be carried out with less risk of transmitting infection.

So that the effect of the pulse wave influencing the measurement is eliminated, the disruption in the aqueous humour excretion can be detected more quickly and more reliably than by the prior known devices and processes. The measurement means that the patient is involved for a shorter time, and hence the device as proposed and also the process is able to provide more accurate measurement results with mass examinations, where the value of the aqueous humour pressure obtained in the course of the tonometric measurement is in the region of boundary cases.

What is claimed is:

1. In an apparatus for determining the aqueous humor pressure of the eye by means of dynamically applied pressure and without direct contact with the eye, said apparatus having means for directing a jet of gas at the eye under examination, said means including, a gas nozzle for positioning adjacent to but spaced apart from the said eye, said gas nozzle having an electrically conductive part facing the said eye, said part forming a first electrode of a capacitor, and a controllable pneumatic unit connected to said gas nozzle, said pneumatic unit supplying a controlled stream of gas to the said nozzle; the improvement which comprises:

capacitative circuit means having a pair of input signal terminals and an output signal terminal, one of said input terminals being connected to the said electrically conductive part of the gas nozzle and the other of said input terminals being connected to the patient whose eye is undergoing examination, said eye forming a second electrode of the said capacitor, said capacitative circuit means being sensitive to changes of capacitance at said input terminals and converting said changes into electrical signals provided at said output terminal;

a sampling and sample-holding circuit having first and second input terminals and an output terminal, said first input terminal being connected to the said output terminal of the capacitative circuit means, said sampling and sample-holding circuit taking samples of the output of the capacitative circuit means under the control of a signal applied to the said second input terminal and providing a signal on the said output terminal representative of the value of the instant sample;

indicating means connected to the said output terminal of said sampling and sample-holding circuit for providing an indication of the value of the instant sample; and control means having a first output terminal and a second output terminal said first output terminal being connected to said second input terminal of said sampling and sample-holding circuit and said second output terminal being connected to said controllable pneumatic unit, said control means providing output signals to control the operation of the said sampling and sample-holding circuit and said controllable pneumatic unit.

2. The apparatus of claim 1, wherein the said nozzle comprises a body formed of dielectric material having a coating of electrically conductive material at least on the portion thereof facing the eye under examination.

3. Apparatus for determining the aqueous humor pressure of the eye by means of dynamically applied pressure and without direct contact with the eye, said apparatus having means for directing a jet of gas at the eye under examination, said means including, a gas nozzle for positioning adjacent to but spaced apart from the said eye, said gas nozzle having an electrically conductive part facing the said eye, said part forming a first electrode of a capacitor, and a controllable pneumatic unit connected to said gas nozzle, said pneumatic unit supplying a controlled stream of gas to the said nozzle; the improvement which comprises:

capacitative circuit means having a pair of input signal terminals and an output signal terminal, one of said input terminals being connected to the said electrically conductive part of the gas nozzle and the other of said input terminals being connected to the patient whose eye is undergoing examination, said eye forming a second electrode of the said capacitor, said capacitative circuit means being sensitive to changes of capacitance at said input terminals and converting said changes into electrical signals provided at said output terminal;

analysing means having an input terminal and an output terminal, said input terminal being connected to the said output terminal of the capacitative circuit means;

control means having a signal input terminal and first, second, and third control signal output terminals, said input terminal being connected to the output terminal of said analysing means and said first control signal output terminal being connected to the pneumatic unit so as to provide control thereof;

a sampling and sample-holding means having first and second input terminals and an output terminal, said first input terminal being connected to the output terminal of the capacitative circuit means, said second input terminal being connected to the said second control signal output terminal of the control means, said sampling and sample-holding means taking samples of the output of the capacitative circuit means under the control of the signal applied to said second input terminal and providing a signal on the said output terminal representative of the value of the instant sample;

a computing unit having first and second input terminals and an output terminal, said first input terminal being connected to said output terminal of the sampling and sample-holding means, said second input terminal being connected to the said third control signal output terminal of the control means; and indicating means connected to the output of the arithmetic unit for providing an indication of the value of the said sample.

4. The apparatus of claim 3, wherein the said nozzle comprises a body formed of dielectric material having a coating of electrically conductive material at least on the portion thereof facing the eye under examination.

5. Apparatus for determining the aqueous humor pressure of the eye by means of dynamically applied pressure and without direct contact with the eye, said apparatus having means for directing a jet of gas at the eye under examination, said means including a gas nozzle for positioning adjacent to but spaced apart from the said eye, said gas nozzle having an electrically conductive part facing the said eye, said part forming a first electrode of a capacitor, and a controllable pneumatic unit connected to said gas nozzle, said pneumatic unit supplying a controlled stream of gas to said nozzle, the improvement which comprises:

capacitative circuit means having a pair of input signal terminals and an output signal terminal, one of said input terminals being connected to the said electrically conductive part of the gas nozzle and the other of said input terminals being connected to the patient whose eye is undergoing examination, said eye forming a second electrode of the said capacitor, said capacitative circuit means being sensitive to changes of capacitance at said input terminals and converting said changes into electrical signals provided at said output terminals;

a pulse sensor for sensing the systaltic rhythm of the person whose eye is being examined;

analysing means having an input terminal and an output terminal, said input terminal being connected to the said pulse sensor;

control means having a signal input terminal and first, second and third control signal output terminals, said input terminal being connected to the output terminal of said analysing means and said first control output terminal being connected to the pneumatic unit so as to provide control thereof;

a sampling and sample-holding means having first and second input terminals and an output terminal, said first input terminal being connected to the output terminal of the capacitative circuit means, said second input terminal being connected to the said second control signal output terminal of the control means, said sample and sample-holding means taking samples of the output of the capacitative circuit means under the control of the signal applied to said second input terminal and providing a signal on the said output terminal representative of the value of the instant sample;

a computing unit having first and second input terminals and an output terminal, said first input terminal being connected to said output terminal of the sampling and sample-holding means, said second input terminal being connected to the said third control signal output terminal of the control means, and indicating means connected to the output of the computing unit for providing an indication of the value of the said sample.

6. The apparatus of claim 5, wherein the said nozzle comprises a body formed of dielectric material having a coating of electrically conductive material at least on the portion thereof facing the eye under examination.

* * * * *